(12) United States Patent
Okamura et al.

(10) Patent No.: US 10,228,363 B2
(45) Date of Patent: Mar. 12, 2019

(54) URINE SAMPLE ANALYZER AND URINE SAMPLE DISPENSING METHOD

(71) Applicant: Sysmex Corporation, Kobe-shi, Hyogo (JP)

(72) Inventors: Yuta Okamura, Kobe (JP); Ryuichiro Ebi, Kobe (JP); Masahiko Oguro, Kobe (JP); Go Senda, Kobe (JP)

(73) Assignee: SYSMEX CORPORATION, Kobe-Shi, Hyogo (JP)

(*) Notice: Subject to any disclaimer, the term of this patent is extended or adjusted under 35 U.S.C. 154(b) by 134 days.

(21) Appl. No.: 15/082,470

(22) Filed: Mar. 28, 2016

(65) Prior Publication Data

US 2016/0290991 A1   Oct. 6, 2016

(30) Foreign Application Priority Data

Mar. 31, 2015 (JP) ................................. 2015-072029

(51) Int. Cl.
*G01N 33/493* (2006.01)
*G01N 1/14* (2006.01)
(Continued)

(52) U.S. Cl.
CPC ............ *G01N 33/493* (2013.01); *B01L 3/508* (2013.01); *B01L 3/52* (2013.01); *G01N 1/14* (2013.01); *G01N 15/1459* (2013.01); *G01N 35/00584* (2013.01); *G01N 35/1004* (2013.01); *G01N 35/1095* (2013.01); *B01L 2200/06* (2013.01);
(Continued)

(58) Field of Classification Search
CPC ......... B01L 2200/06; B01L 2300/0636; B01L 2400/049; B01L 3/508; B01L 3/52; G01N 15/1459; G01N 1/14; G01N 2015/0065; G01N 2035/1032; G01N 2333/4737; G01N 33/493; G01N 35/00584; G01N 35/1004; G01N 35/1095

See application file for complete search history.

(56) References Cited

U.S. PATENT DOCUMENTS 6,383,452 B1 * 5/2002 Miyake ................ G01N 35/028
422/504
8,741,218 B2 * 6/2014 Saito .................. G01N 21/6428
422/500

(Continued)

FOREIGN PATENT DOCUMENTS

EP   2 397 861 A1   12/2011
EP   2 554 997 A1   2/2013

*Primary Examiner* — Samuel P Siefke
(74) *Attorney, Agent, or Firm* — Brinks Gilson & Lione

(57) ABSTRACT

Disclosed is a sample dispensing method. The method comprises: suctioning a urine sample from a sample container by a first nozzle; moving the first nozzle to a holding chamber after the first nozzle has suctioned the urine sample from the sample container, and discharging the urine sample into the holding chamber; moving the first nozzle to a first wash tank and washing the first nozzle in the first wash tank after the first nozzle has discharged the urine sample into the holding chamber; and moving a second nozzle to the holding chamber after the first nozzle has started moving to the first wash tank, and moving the second nozzle which has suctioned the urine sample from the holding chamber to respective plurality of processing chambers and discharging a part of the urine sample to the respective plurality of processing chambers.

19 Claims, 12 Drawing Sheets

(51) Int. Cl.
  *B01L 3/00* (2006.01)
  *G01N 35/10* (2006.01)
  *G01N 35/00* (2006.01)
  *G01N 15/14* (2006.01)
  *G01N 15/00* (2006.01)

(52) U.S. Cl.
  CPC . *B01L 2300/0636* (2013.01); *B01L 2400/049* (2013.01); *G01N 2015/0065* (2013.01); *G01N 2035/1032* (2013.01)

(56) References Cited

U.S. PATENT DOCUMENTS

2013/0131859 A1* 5/2013 Takai ................ G01N 35/0092
  700/214
2014/0322802 A1  10/2014 Takemoto \* cited by examiner

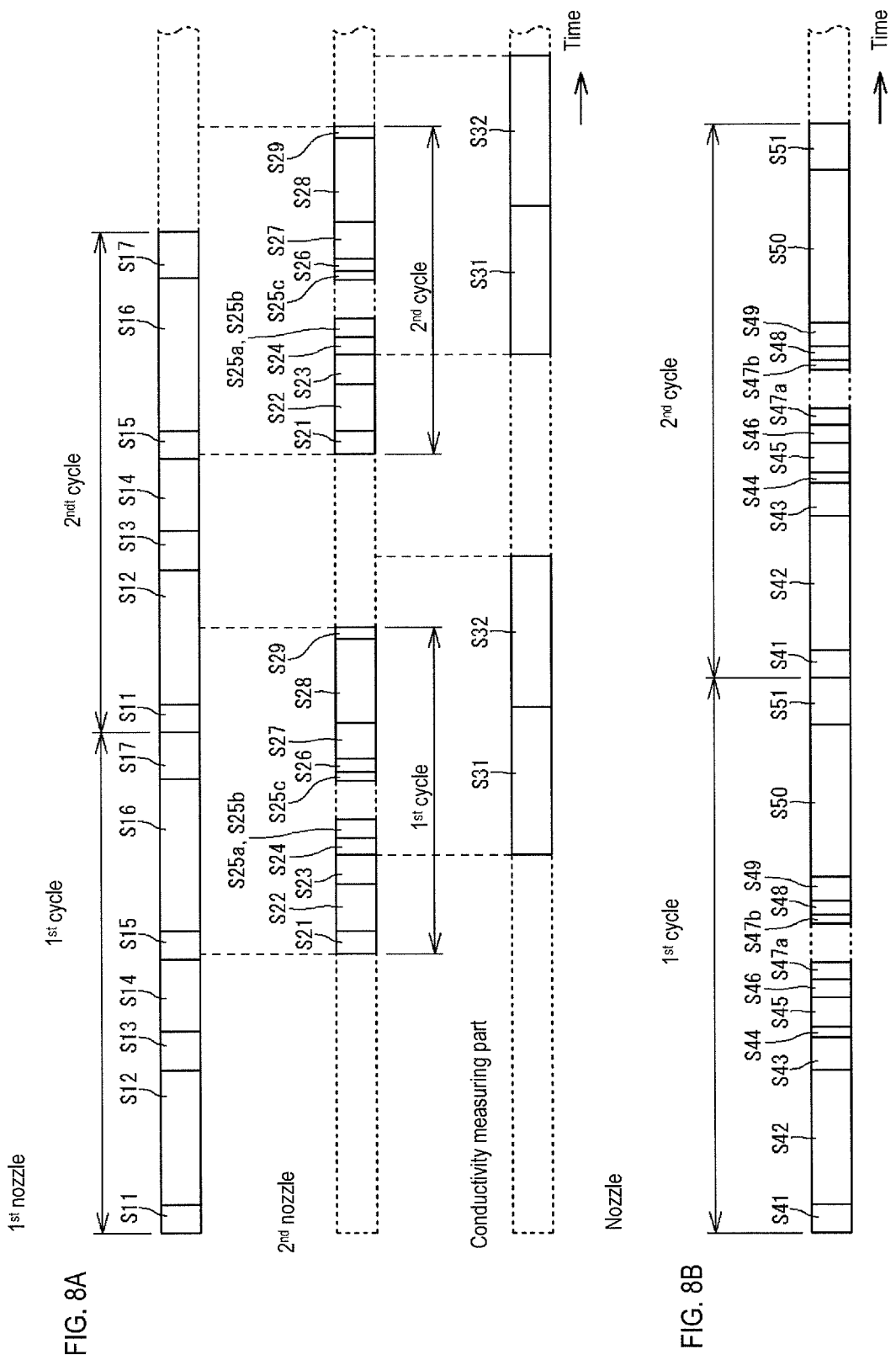

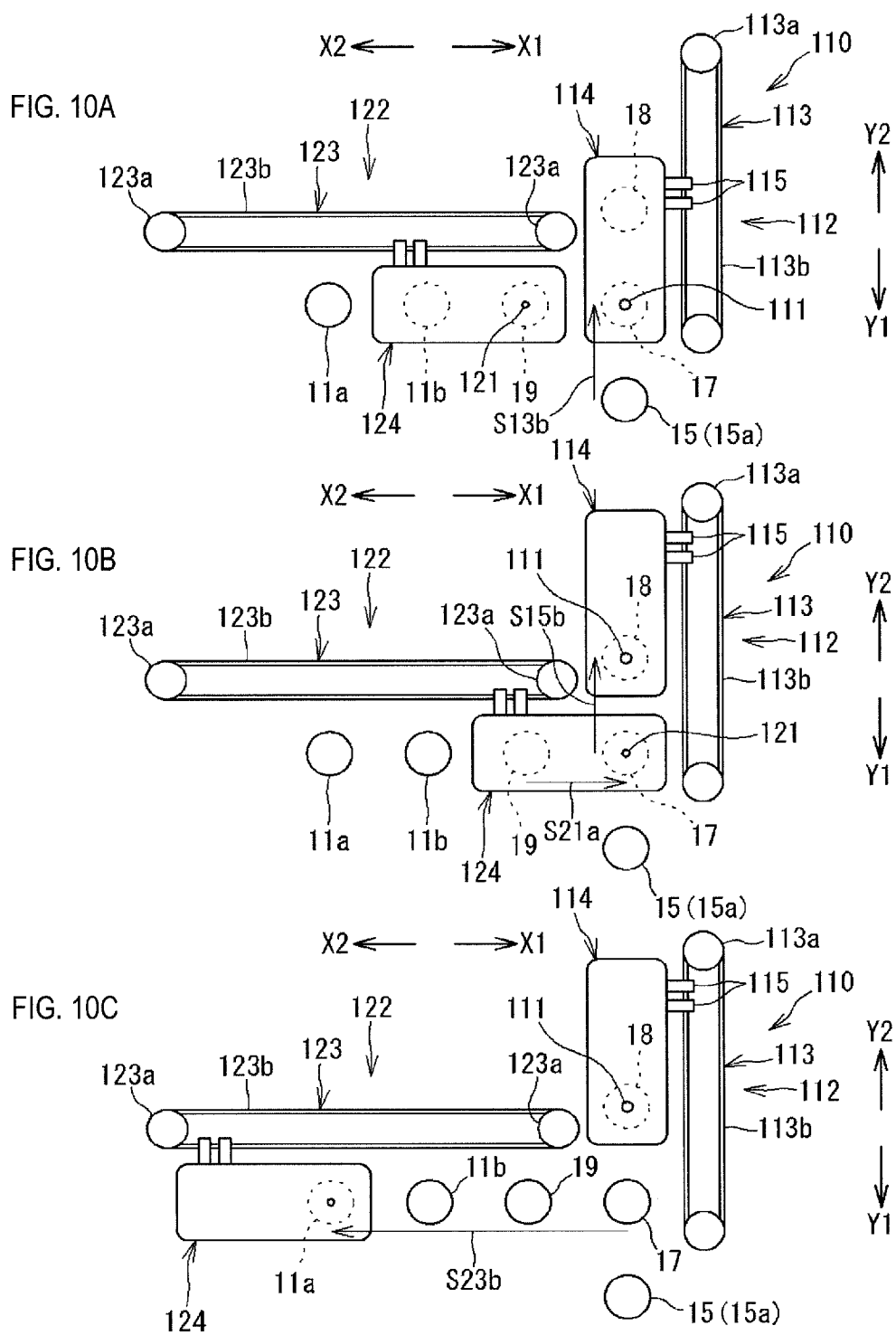

URINE SAMPLE ANALYZER AND URINE SAMPLE DISPENSING METHOD

RELATED APPLICATIONS

This application claims priority from prior Japanese Patent Application No. 2015-072029, filed on Mar. 31, 2015, entitled "URINE SAMPLE ANALYZER AND URINE SAMPLE DISPENSING METHOD", the entire contents of which are incorporated herein by reference.

BACKGROUND OF THE INVENTION

1. Field of the Invention

The invention relates to a urine sample analyzer and urine sample dispensing method.

2. Description of the Related Art

United States Patent Application Publication No. 2014/0322802 discloses a device in which a single sampling nozzle suctions and discharges sample in order to dispense the sample.

When measuring a plurality of samples, the nozzle must be washed each time the nozzle finishes suctioning and discharging a sample to prevent mutual contamination of samples. United States Patent Application Publication No. 2014/322802 also discloses washing the sampling nozzle which has finished dispensing a sample.

However, when the nozzle is washed, the nozzle cannot suction the next sample until the washing of the nozzle is completed. As a result, when measuring a plurality of samples, more time is required until the measurement results for the plurality of sample is reported due to the waiting time for washing the nozzle.

SUMMARY OF THE INVENTION

The scope of the present invention is defined solely by the appended claims, and is not affected to any degree by the statements within this summary.

One aspect of the invention relates to a urine sample analyzer. The analyzer comprises: a holding chamber for holding a urine sample; a first nozzle for suctioning a urine sample from a sample container and discharging the suctioned urine sample into the holding chamber; a first wash tank for washing the first nozzle; a plurality of processing chambers for receiving and processing a urine sample; a second nozzle for suctioning the urine sample from the holding chamber and respectively discharging a part of the suctioned urine sample to the plurality of holding chambers; and a controller. The controller is configured to perform operations for: moving the first nozzle to the first wash tank and washing the first nozzle in the first wash tank after the first nozzle has discharged a urine sample into the holding chamber; and moving the second nozzle to the holding chamber after the first nozzle has started moving from the holding chamber to the first wash tank, moving the second nozzle which has suctioned the urine sample from the holding chamber to the respective plurality of processing chambers, and discharging a part of the urine sample from the second nozzle into the respective plurality of processing chambers. The analyzer further comprises: a detector for detecting information of material components in the urine samples respectively processed in the plurality of processing chambers; and an analyzing part for analyzing the information of the material components detected by the detector.

Another aspect of the invention relates to a urine sample analyzer. The analyzer comprises: a holding chamber for holding a urine sample; a first nozzle for suctioning a urine sample from a sample container and discharging the suctioned urine sample into the holding chamber; a first wash tank for washing the first nozzle; a plurality of processing chambers for receiving and processing a urine sample; a second nozzle for suctioning the urine sample from the holding chamber and respectively discharging a part of the suctioned urine sample to the plurality of holding chambers; a second wash tank for washing the second nozzle; a detector for detecting information of material components in the urine samples respectively processed in the plurality of processing chambers; and an analyzing part for analyzing the information of material components detected by the detector. A first movement path of the first nozzle and a second movement path of the second nozzle intersect; the holding chamber is arranged at a position of intersection of the first movement path and the second movement path; and the holding chamber is arranged nearer the sample container than the first wash tank in the first movement path.

Another aspect of the invention relates to a sample dispensing method. The method comprises: suctioning a urine sample from a sample container by a first nozzle; moving the first nozzle to a holding chamber after the first nozzle has suctioned the urine sample from the sample container, and discharging the urine sample into the holding chamber; moving the first nozzle to a first wash tank and washing the first nozzle in the first wash tank after the first nozzle has discharged the urine sample into the holding chamber; and moving a second nozzle to the holding chamber after the first nozzle has started moving to the first wash tank, and moving the second nozzle which has suctioned the urine sample from the holding chamber to respective plurality of processing chambers and discharging a part of the urine sample to the respective plurality of processing chambers.

BRIEF DESCRIPTION OF THE DRAWINGS

FIGS. 8A and 8B are timing sequences showing the operation of the sample analyzer;

FIGS. 10A, 10B and 10C illustrate the positions of the first nozzle and the second nozzle;

DETAILED DESCRIPTION OF THE PREFERRED EMBODIMENTS

1. Structure of the Sample Analyzer

Figure 1:
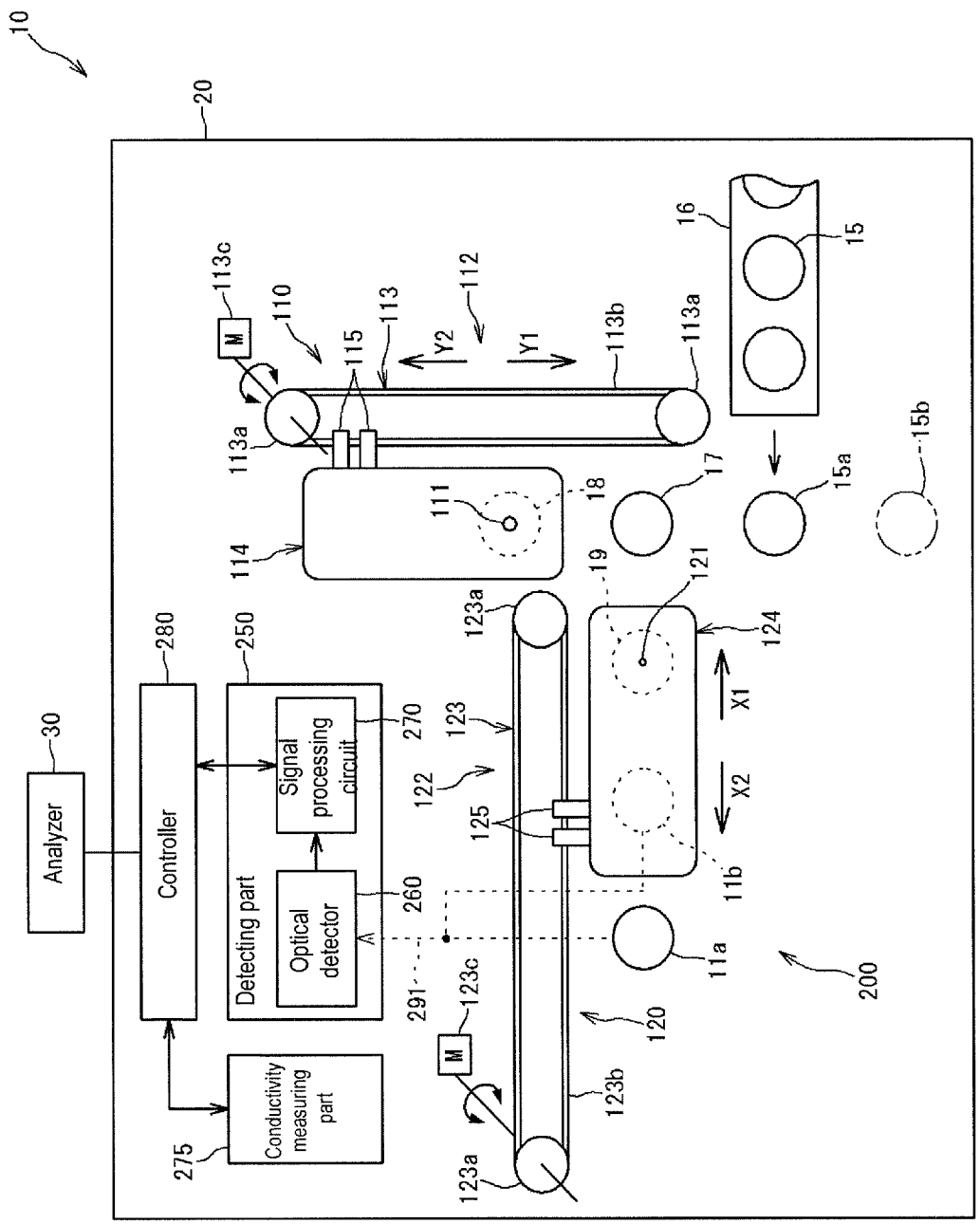
FIG. 1 is a structural view of the sample analyzer.

The sample analyzer 10 shown in FIG. 1 analyzes samples such as urine samples. The sample analyzer 10 includes a measuring unit 20 which measures samples, and an analyzing part 30 which analyzes the output of the measuring unit

20. The measuring unit 20 includes a dispensing part 200, detecting part 250, conductivity measuring part 275, and controller 280.

The dispensing part 200 suctions sample from the sample container 15 which was moved to the sample suctioning position 15*a*, and dispenses the sample in the sample container 15 to the processing chambers 11*a* and 11*b*. The detecting part 250 detects information of the components in the sample. The detecting part 250 includes an optical detector 260 and a signal processing circuit 270. The optical detector 260 performs optical detection on the sample. The signal processing circuit 270 processes the signals output from the optical detector 60, and sends the processed signals to the controller 280. The conductivity measuring part 275 measures the conductivity of the sample and outputs the measurement to the controller 280. The controller 280 controls each part of the measuring unit 20, and communicates with the analyzing part 30. The controller 280 sends the information output from the detecting part 250 and the conductivity measuring circuit 275 to the analyzing part 30. The controller 280 is configured by a microcomputer.

The analyzing part 30 analyzes the information of the components detected by the detecting part 250 and the conductivity of the sample measured by the conductivity measuring part 275. The components in the sample analyzed by the analyzing part 30 are, for example, material components of urine. Material components of urine include, for example, red blood cells, white blood cells, epithelial cells, casts, bacteria, atypical cells, and white blood cell aggregate. When the sample is a urine sample, the conductivity itself is output from the analyzing part as the analysis result. Conductivity can be used to correct other analysis results.

The analyzing part 30 is configured by a computer which has a CPU and memory. A computer program for analyzing the output of the detecting part 250 and the conductivity measuring part 275 is installed in the analyzing part 30.

Figure 2:
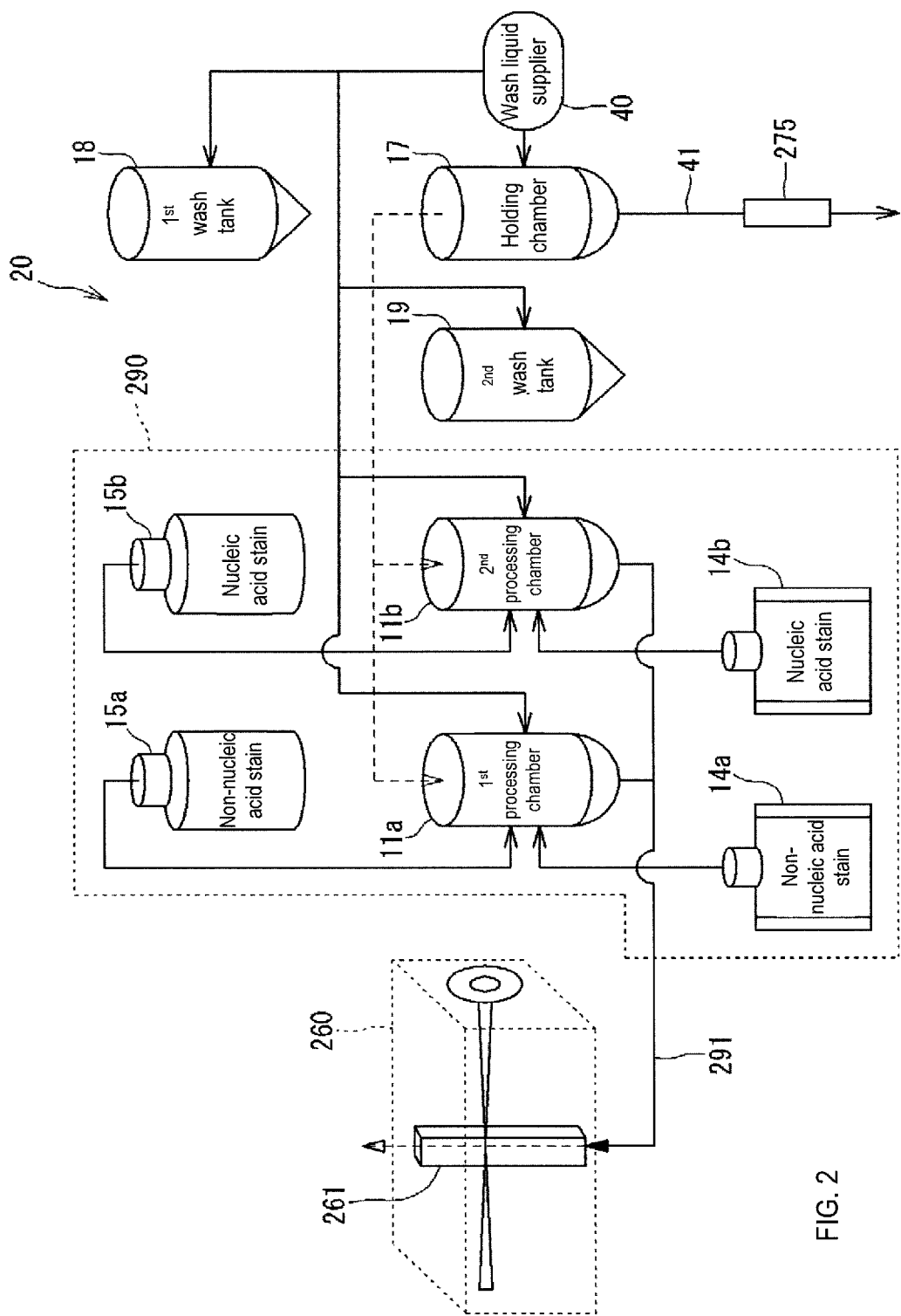
FIG. 2 is a structural view of the preparing part.

As shown in FIG. 2, the measuring unit 20 also has a preparing part 290 for preparing a measurement sample from a sample. The preparing part 290 respectively mixes the urine sample and reagent in a plurality of processing chambers 11*a* and 11*b* to which urine sample is dispensed by the dispensing part 200. The plurality of processing chambers 11*a* and 11*b* include a first processing chamber 11*a* which performs processing to prepare a first measurement sample, and a second processing chamber 11*b* which performs processing to prepare a second measurement sample. The number of processing chambers also may be three or more.

The first measurement sample is obtained by mixing the sample and first reagents 15*a* and 14*a* in the first processing chamber 11*a*. The first reagents 15*a* and 14*a* are, for example, diluting liquid 15*a* and stain 14*a*. The stain 14*a* includes a fluorescent dye which stains material components that do not contain nucleic acid. In the first measurement sample, the material components in the urine are stained by the stain 14*a*. The first measurement sample is used to analyze particles that do not contain nucleic acid, such as red blood cells and casts in urine. The second measurement sample is obtained by mixing the sample and second reagents 15*b* and 14*b* in the second processing chamber 11*b*. The second reagents 15*b* and 14*b* are, for example, diluting liquid 15*b* and stain 14*b*. The stain 14*b* includes dye which stains nucleic acid. In the second measurement sample, the material components in the urine sample are stained by the stain 14*b*. The second measurement sample is used to analyze cells which contain nucleic acid, such as white blood cells, skin cells, fungi, bacteria, and atypical cells in urine.

The first processing chamber 11*a* and second processing chamber 11*b* are connected by a sample delivery path 291 to the flow cell 261 which has the optical detector 260. The first measurement sample is supplied from the first processing chamber 11*a* to the flow cell 261 through the sample delivery path 291. The second measurement sample is supplied from the second processing chamber 11*b* to the flow cell 261 through the sample delivery path 291. The supplied measurement sample flows through the interior of the flow cell 261. The measurement samples are supplied to the flow cell 261 with the first measurement sample being first and the second measurement sample following after the first measurement sample. The supplying of the measurement samples from the processing chambers 11*a* and 11*b* to the flow cell 261 is performed by the controller 280 controlling a pressure source and valves which are not shown in the drawing.

Figure 3:
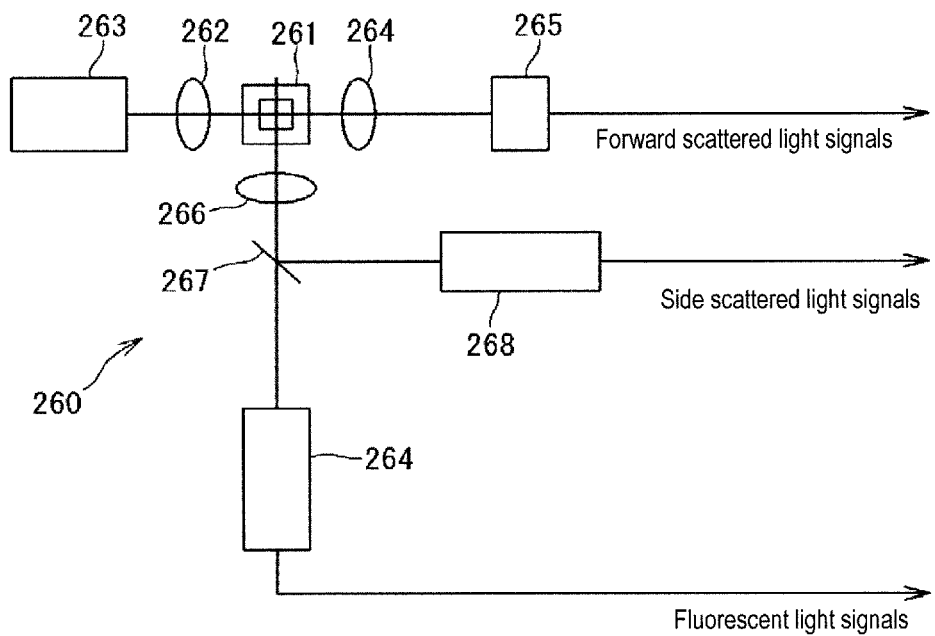
FIG. 3 is a structural view of the optical detecting part.

As shown in FIG. 3, the optical detector 260 is provided with a light irradiating part 263, and plurality of light receiving parts 265, 268, 269, in addition to the flow cell 261. The light irradiating part 263 is configured by, for example, a semiconductor laser light source. The light irradiating part 263 irradiates laser light on the measurement sample flowing through the flow cell 261. The plurality of light receiving parts 265, 268, 269 include a first scattered light receiving part 265, second scattered light receiving part 268, and fluorescent light receiving part 269. The light receiving parts 265, 268, 269 receive light given off from the components in the measurement sample which is irradiated by light.

The optical detector 260 is further provided with a condenser lens 262, collective lenses 264 and 266, and dichroic mirror 267. The condenser lens 262 collects the laser light emitted from the light irradiating part 263, and forms a beam spot on the measurement sample in the flow cell 261. The collective lens 264 collects the forward scattered light given off by the material components in the measurement sample into the first scattered light receiving part 265. The collective lens 266 collects the side scattered light and fluorescent light given off by the material components into the dichroic mirror 267. The dichroic mirror 267 reflects the side scattered light toward the second scattered light receiving part 268, and transmits the fluorescent light toward the fluorescent light receiving part 269.

The light receiving parts 265, 268, and 269 convert the received optical signals to electrical signals. The first scattered light receiving part 265 outputs forward scattered light signals, the second scattered light receiving part 268 outputs side scattered light signals, and the fluorescent light receiving part 269 outputs fluorescent light signals. Each signal represents temporal changes of the intensity of the light. Each signal is supplied to the signal processing circuit 270 shown in FIG. 1 through an amplifier and A/D converter (not shown in the drawing). The signal processing circuit 270 extracts characteristics parameters from each signal to be used in the analysis process performed by the analyzing part 30. The characteristics parameters include, for example, forward scattered light intensity, forward scattered light pulse width, side scattered light intensity, fluorescent light intensity, fluorescent light pulse width, and fluorescent light pulse area. The characteristics parameters are sent to the analyzing part 30 through the controller 280.

Returning to FIG. 2, the measuring unit 20 also is provided with a holding chamber 17 which temporarily holds the sample until the sample suctioned from the sample container is dispensed to the processing chambers 11a and 11b, a first wash tank 18 for washing the first nozzle 111, a second wash tank 19 for washing the second nozzle 121, and a wash liquid supplier 40 for supplying wash liquid to the holding chamber 17. The wash liquid supplier 40 also supplies wash liquid to the first wash tank 18 and the second wash tank 19. The wash liquid supplier 40 also supplies wash liquid to other locations which require washing, such as the first processing chamber 11a and the second processing chamber 11b.

As shown in FIG. 2, the previously mentioned conductivity measuring part 275 is connected to the holding chamber 17 through a flow path 41. During conductivity measurement of a sample, the sample held in the holding chamber 17 is drawn to the conductivity measuring part 275.

2. Structure of the Dispensing Part

Returning to FIG. 1, the dispensing part 200 is provided with a first unit 110 and second unit 120 for dispensing the sample suctioned from the sample container 15 into the plurality of processing chambers 11a and 11b. The first unit 110 includes a first nozzle 111 for suctioning and discharging a sample, and a first drive part 112 for moving the first nozzle 111. The second unit 120 includes a second nozzle 121 for suctioning and discharging a sample, and a second drive part 122 for moving the second nozzle 121. The first drive part 112 and second drive part 122 are controlled by the controller 280.

The first nozzle 111 has an inlet 111a on the bottom end, such that sample is suctioned from the sample container 15, and the suctioned sample is discharged from the inlet 111a into the holding chamber 17. The sample container 15 is held in a sample rack 16. The sample rack 16 is transported by a transport device which is not shown in the drawing, so that the sample container 15 is moved to the sample suction position 15a. The first nozzle 111 can suction sample from the sample container 15 disposed at the sample suction position 15a.

The measuring unit 20 of FIG. 1 also has an urgent sample suction position 15b at which an urgent sample container may be set, and the first nozzle 111 can suction sample from the sample container 15 disposed at the urgent sample suction position 15b when a sample container is set at the urgent sample suction position 15b.

The first drive part 112 includes a first horizontal mover 113 which moves the first nozzle 111 in horizontal directions, and a first vertical mover 114 which moves the first nozzle 111 in vertical directions. The first horizontal moving device 113 has an endless belt 113b wound around a pair of pulleys 113a. The first vertical mover 114 is mounted on the endless belt 113a through an attachment 115. The first nozzle 111 is provided on the first vertical mover 114. The pulley 113a is driven to rotate by a motor 113c. The motor 113c is controlled by the controller 280. When the pulleys 113a are driven to rotate, the endless belt 113b rotates and the first vertical mover 114 and the first nozzle 111 move in a first horizontal direction, that is, the Y1 direction or the Y2 direction. Note that the Y1 direction is the front part of the sample analyzer 10, and the Y2 direction is the back part of the sample analyzer 10. The Y1 direction and the Y2 direction are collectively referred to as the Y direction. The Y direction is the front and back direction of the sample analyzer 10.

Figure 4A:
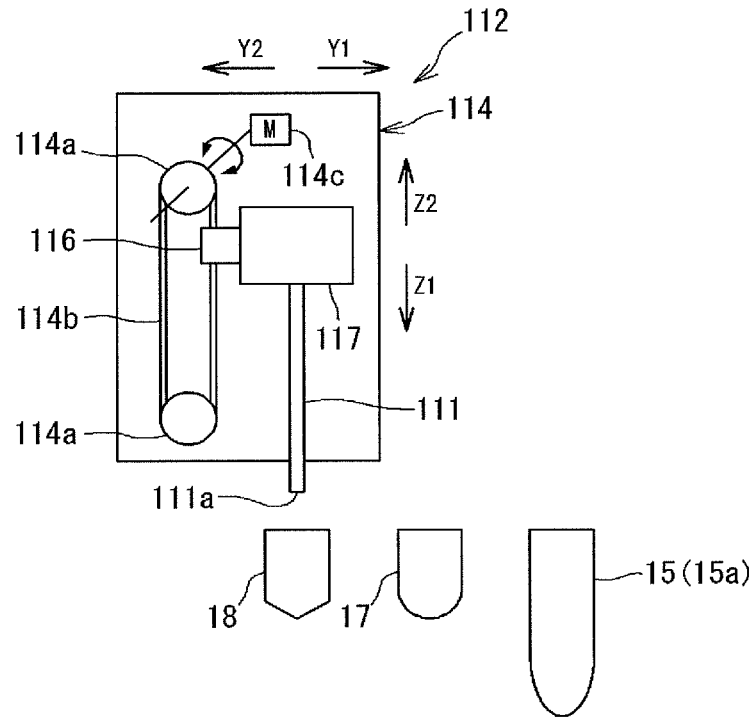
FIGS. 4A and 4B are structural views of the first vertical mover and second vertical mover.

The first vertical mover 114 has an endless belt 114b wound around a pair of pulleys 114a, as shown in FIG. 4A. A first nozzle holder 117 for holding the first nozzle 111 is mounted on the endless belt 114b through an attachment 116. The pulley 114a is driven to rotate by a motor 114c. The motor 114c is controlled by the controller 280. When the pulleys 114a are driven to rotate, the endless belt 114b rotates and the first nozzle 111 held by the first nozzle holder 117 moves in a vertical direction, that is, the Z1 direction or Z2 direction. Note that the Z1 direction is the lower part of the sample analyzer 10, and the Z2 direction is the upper part of the sample analyzer 10. The Z1 direction and the Z2 direction are collectively referred to as the Z direction. The Z direction is the up and down direction of the sample analyzer 10.

The second nozzle 121 has an inlet 121a on the bottom end, such that sample is suctioned from the holding chamber 17, and part of the suctioned sample is discharged from the inlet 121a into the first processing chamber 11a, and another part of the suctioned sample is discharged into the second processing chamber 11b. Accordingly, part of the sample is used in the process of preparing the first measurement sample, and another part of the sample is used in the process of preparing the second measurement sample among the entire amount of the sample separately discharged twice from the second nozzle 121.

The second drive part 122 includes a second horizontal mover 123 which moves the second nozzle 121 in horizontal directions, and a second vertical mover 124 which moves the second nozzle 121 in vertical directions. The second horizontal mover 123 has an endless belt 123b wound around a pair of pulleys 123a. The second vertical mover 124 is mounted on the endless belt 123a through an attachment 125. The second nozzle 121 is provided on the second vertical mover 124. The pulley 123a is driven to rotate by a motor 123c. The motor 123c is controlled by the controller 280. When the pulleys 123a are driven to rotate, the endless belt 123b rotates and the second vertical mover 124 and the second nozzle 121 move in a second horizontal direction, that is, the X1 direction or the X2 direction. Note that the X1 direction is on the right side viewed from the front of the sample analyzer 10, and the X2 direction is on the left side viewed from the front of the sample analyzer 10. The X direction is the side to side direction of the sample analyzer 10.

Figure 4B:
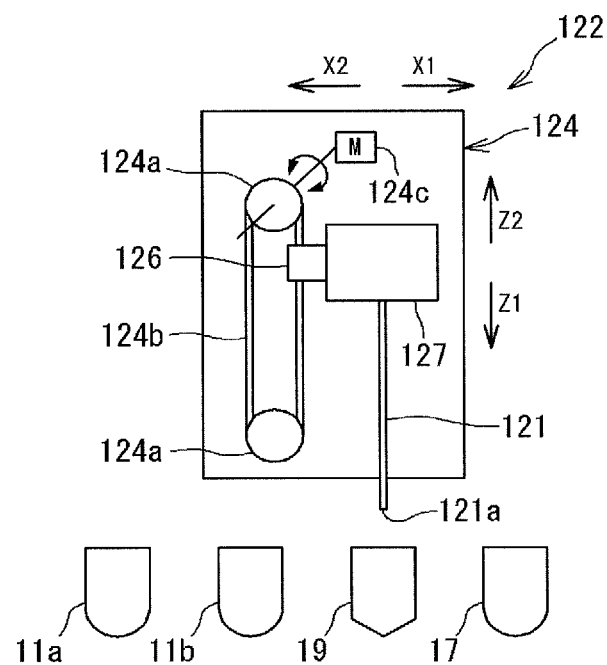

The second vertical mover 124 has an endless belt 124b wound around a pair of pulleys 124a, as shown in FIG. 4B. A second nozzle holder 127 for holding the second nozzle 121 is mounted on the endless belt 124b through an attachment 126. The pulley 124a is driven to rotate by a motor 124c. The motor 124c is controlled by the controller 280. When the pulleys 124a are driven to rotate, the endless belt 124b rotates and the second nozzle 121 held by the second nozzle holder 127 moves in a vertical direction, that is, the Z1 direction or Z2 direction.

Although the first drive part 112 and second drive part 122 move the nozzles 111 and 121 by a belt drive system, the nozzles 111 and 121 also may be moved by another drive system. Examples of other drive systems are systems that have a mechanism for moving by rotation of a screw shaft, or systems that have a mechanism for running a rotationally driven roller on a guide rail.

Figure 5:
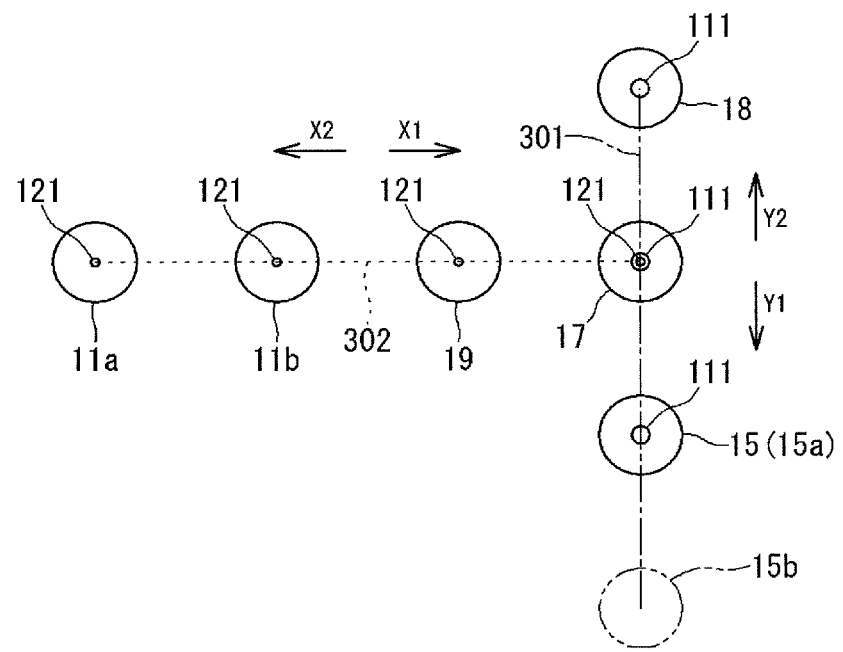
FIG. 5 illustrates the layout of the holding chamber, processing chambers, and wash tanks.

As shown in FIG. 5, the sample suctioning position 15a at which the sample container 15 is set, the holding chamber 17, and the first wash tank 18 are arranged on a straight line in the front to back Y direction. The urgent sample suctioning position 15b is arranged at a position extended in the front direction on a straight line from the holding chamber 17 and sample suctioning position 15a. The holding chamber 17 is arranged at a position nearer the sample suctioning position 15a at which the sample container 15 is set than the first wash tank 18. The first nozzle 111 can move to the position of the sample suctioning position 15a, urgent sample suctioning position 15b, holding chamber 17, and first wash tank 18 by the first horizontal mover 113. A first moving path 301 of the first nozzle 111 by the first horizontal mover 113 is a straight line path along the Y direction. The first moving path 301 also may be a curved path.

In the present embodiment, the first nozzle 111 can rapidly move from the position of the sample container 15 to the position of the holding chamber 17 since the holding chamber 17 is arranged at a position near the sample suctioning position 15a.

Figure 6:
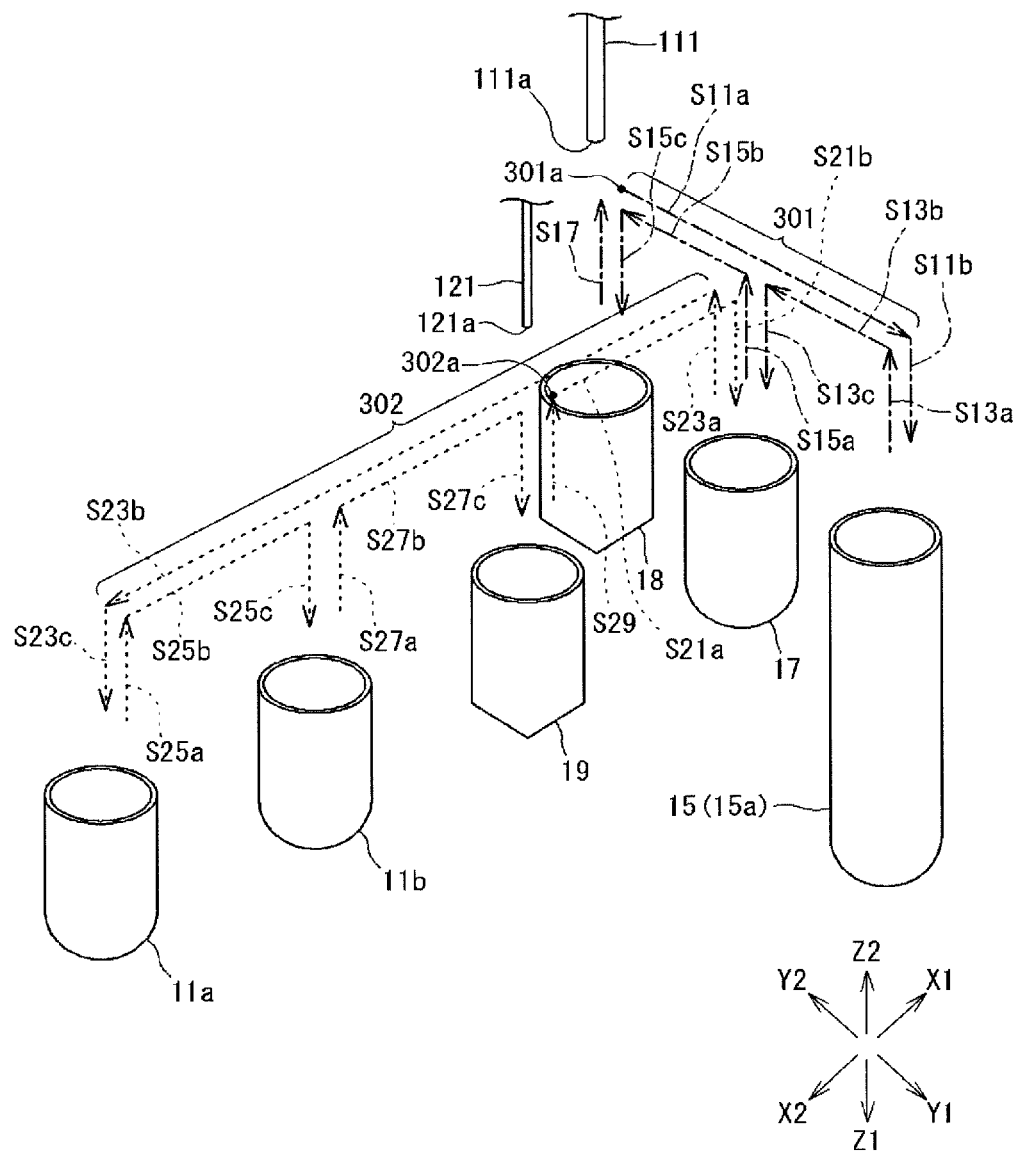
FIG. 6 illustrates the nozzle movement paths.

The first vertical mover 114 lifts the first nozzle 111 to the position of the sample suctioning position 15a at which the sample container 15 is set, the holding chamber 17, and the first wash tank 18, as shown in FIG. 6. Although omitted in FIG. 6, the first vertical mover 114 can lift the first nozzle 111 in the Z direction at the urgent sample suctioning position 15b.

The first nozzle 111 enters the sample container 15, holding chamber 17, or first wash tank 18 by descending. The first nozzle 111 retracts from the sample container 15, holding chamber 17, or first wash tank 18 by ascending. The movement of the first nozzle 111 shown in FIG. 6 is performed by the controller 280 controlling the first drive part 112.

Returning to FIG. 5, The second wash tank 19, first processing chamber 11a, and second processing chamber 11b are aligned on a straight line in the X direction which intersects the Y direction with the holding chamber 17 as the starting point. The second wash tank 19 is arranged at a position nearer the holding chamber 17 than either of the plurality of processing chambers 11a and 11b. Thus, after washing in the second wash tank 19, the second nozzle 121 can be prevented from passing above the processing chambers 11a and 11b. Wash liquid may adhere and remain on the second nozzle 121 after washing in the second wash tank 19. Therefore, there is concern that the wash liquid may contaminate the processing chamber 11a and 11b when the second nozzle 121 passes over the processing chambers 11a and 11b. In the present embodiment, wash liquid on the second nozzle 121 is prevented from contaminating the processing chambers 11a and 11b.

The first processing chamber 11a is provided on the X2 side from the second processing chamber 11b. The second nozzle 121 can move to the position of the holding chamber 17, second wash tank 19, first processing chamber 11a and second processing chamber 11b by the second horizontal mover 123. A second moving path 302 of the second nozzle 121 by the second horizontal mover 123 is a straight line path along the X direction. The second moving path 302 also may be a curved path. The second moving path 302 intersects the first moving path 301 at the position of the holding chamber 17. In other words, the holding chamber 17 is arranged at the position of intersection of the first moving path 301 and the second moving path 302. Therefore, sample is easily dispensed through coordination of the first nozzle 111 and second nozzle 121. Although the first moving path 301 and second moving path 302 intersect, both paths 301 and 302 are straight line paths and compact since they are perpendicular.

The second vertical mover 124 raises the second nozzle 121 in the Z direction to the positions of the holding chamber 17, second wash tank 19, second processing chamber 11b, and first processing chamber 11a, as shown in FIG. 6. The second nozzle 121 enters inside the holding chamber 17, second wash tank 19, second processing chamber 11b, and first processing chamber 11a by descending. The second nozzle 121 is retracted from the holding chamber 17, second wash tank 19, second processing chamber 11b, and first processing chamber 11a by ascending. The movement of the first nozzle 111 shown in FIG. 6 is performed by the controller 280 controlling the second drive part 122.

Figure 7:
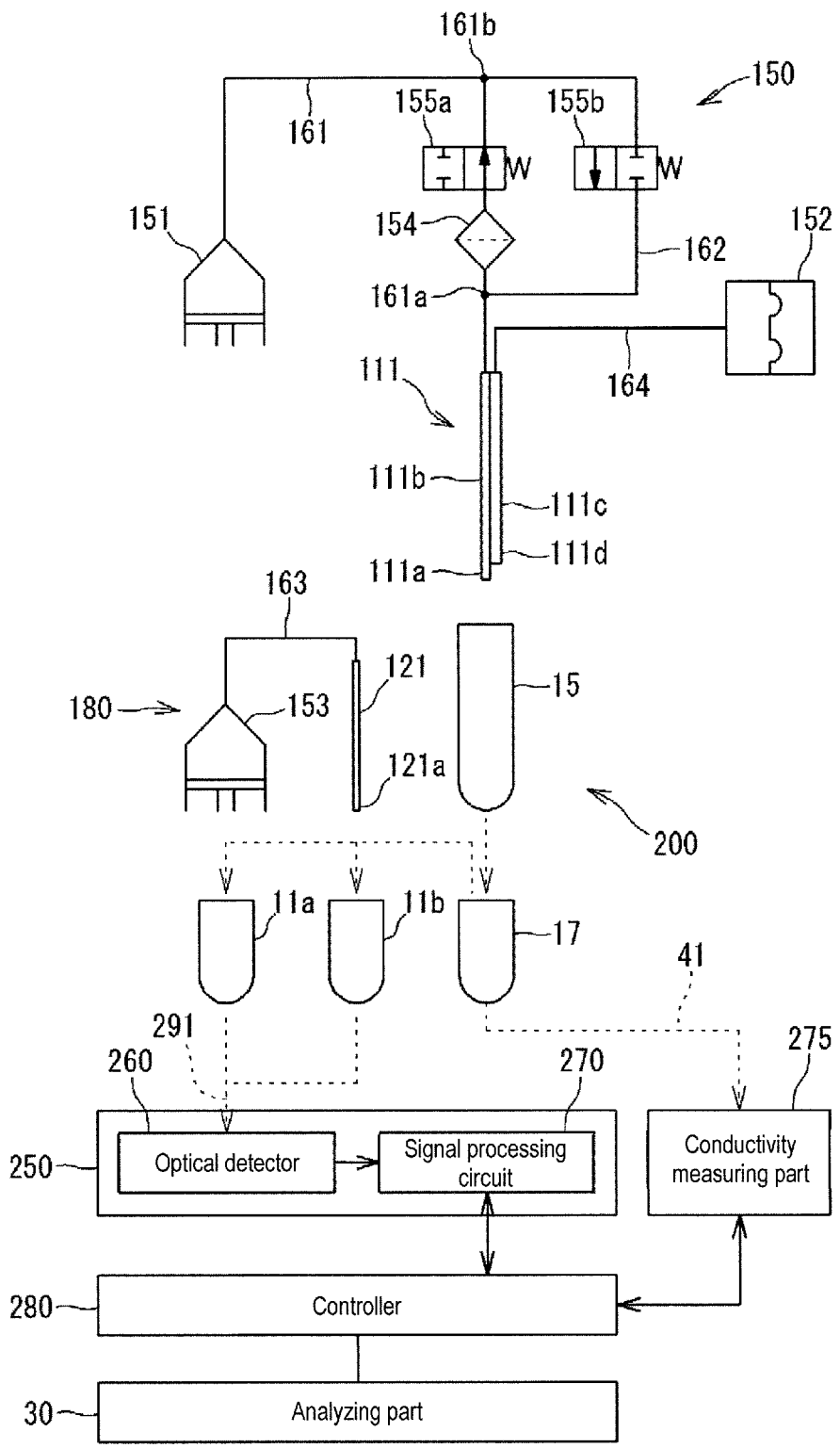
FIG. 7 is a structural view of the suction circuit and dispensing circuit.

The dispensing part 200 further includes a sample suctioning circuit 150 for suctioning the sample through the first nozzle 111, and a dispensing circuit 180 for dispensing the sample to the processing chambers 11a and 11b through the second nozzle 121, as shown in FIG. 7. The sample suctioning circuit 150 and dispensing circuit 180 are configured as fluid circuits. The fluid circuit of the embodiment is a pneumatic circuit.

The sample suctioning circuit 150 includes a first pressure source 151, a first flow path 161 from the first nozzle 111 to the first pressure source 151, and a second flow path 162 which branches off from the first flow path 161. The first pressure source 151 is, for example, a syringe pump. The dispensing circuit 180 includes a pressure source 153, and a third flow path 163 from the second nozzle 121 to the pressure source 153. The pressure source 153 is, for example, a syringe pump.

The first nozzle 111 of the embodiment is configured to integratedly have a suctioning nozzle 111b and mixing nozzle 111c. The suctioning nozzle 111b and mixing nozzle 111c respectively have suction ports 111a and 111d at the lower end, and are respectively capable of suctioning and discharging sample from the suction ports 111a and 111d. The previously mentioned first flow path 161 is connected to the suction nozzle 111b. The sample suctioning circuit 150 is also provided with a second pressure source 152, and a fourth flow path 164 from the mixing nozzle 111c to the second pressure source 152. The second pressure source 152 is, for example, a diaphragm pump.

The second flow path 162 shown in FIG. 7 is a bypass path which branches from the first flow path 161 at a first position 161a of the first flow path 161, and conjoins the first flow path 161 at a second position 161b on the first pressure source 151 side from the first position 161a. A filter 154 for capturing foreign matter is provided between the first position 161a and 161b in the first flow path 161. Foreign matter in the urine sample suctioned from the suction nozzle 111b can be captured by the filter 154. Foreign matter contaminating a urine sample may include tissue paper fragments, pubic hair and the like.

A first valve 155a is provided between the first position 161a and second position 161b of the first flow path 161. A second valve 155b is provided in the second flow path 162. The first valve 155a and the second valve 155b are, for example, solenoid valves. The first valve 155a and the second valve 155b switch the flow of sample being suctioned/discharged by the suction nozzle 111b. The operation of the first valve 155a and second valve 155b, and operation of the pressure sources 151, 152, and 153 is controlled by the controller 280.

As shown in FIG. 7, the first valve 155a is in an open state when degaussed and in a closed state during excitation. The second valve 155b is in a closed state when degaussed and in an open state during excitation. Both valves 155a and 155b are degaussed when a urine sample is suctioned from a sample container 15. The urine sample is suctioned from the suction nozzle 111b by the suction pressure generated by the first pressure source 151. At this time, the suctioned urine sample is drawn through the first flow path 161 which has the open first valve 155a to the first pressure source 151 side and not the second flow path 162 which has the closed second valve 155b. The entirety of the suctioned urine sample moves past the second position 161b to the first pressure source 151 side. Since the suctioned urine sample passes through the filter 154 provided in the first flow path 161, foreign matter is captured by the filter 154.

Both valves 155a and 155b are excited when the suctioned urine sample is being discharged. The sample which has passed through the filter 154 and is between the second position 161b and the first position 161a is discharged from the suction nozzle 111b by the discharge pressure generated by the first pressure source 151. At this time, the sample bypasses the filter 154 by passing through the second flow path 162 which has the open second valve 155b and not through the first flow path 161 which has the closed first valve 155a. During sample discharge, foreign matter captured by the filter 154 is prevented from being discharged from the nozzle 111b along with the urine sample by bypassing the filter 154.

The mixing nozzle 111c mixes the sample in the sample container 15 before the urine sample is suctioned from the sample container 15. The sample is allowed to flow from the mixing nozzle 111c to the fourth flow path 164 by the suction pressure generated by the second pressure source 152, then the sample in the fourth flow path 164 is again returned from the mixing nozzle 111c to the sample container 15 by the discharge pressure generated by the second pressure source 152. The sample is thoroughly mixed by the repeated suction and discharge by the mixing nozzle 111c. The fourth flow path 164 is a formed as a wider flow path than the first flow path 161 and second flow path 162. Thus, the suction and discharge for mixing is performed efficiently.

Although a syringe pump suited to provide a precise amount of sample is used as the first pressure source 151, a diaphragm pump is used as the second pressure source 152 in the embodiment. The diaphragm pump 152 can perform the mixing in a short time since its suction and discharge speeds are faster and several suctions and discharges can be performed quickly.

The dispensing circuit 180 suctions the sample in the holding chamber 17 through the second nozzle 121, and dispenses the suctioned sample to the processing chambers 11a and 11b. The sample in the holding chamber 17 is allowed to flow from the second nozzle 121 to the third flow path 163 by the suction pressure generated by the pressure source 153. Thereafter, the sample in the third flow path 163 is discharged to the plurality of processing chambers 11a and 11b by the discharge pressure generated by the pressure source 153. The dispensing circuit 180 does not require a filter 154 to capture foreign matter in the third flow path 163 since the sample is suctioned after the foreign matter has been removed. That is, the third flow path 163 is a filterless flow path.

The second nozzle 121 is configured to have an internal diameter that is smaller than the flow path diameter within the suctioning nozzle 111a of the first nozzle 111. Sample possibly containing foreign matter can be efficiently suctioned by enlarging the suctioning nozzle 111a. However, a precise amount of sample can be obtained by narrowing the second nozzle 121. The second nozzle 121 has a low possibility of becoming clogged by foreign matter even if narrowed because foreign matter has been removed from the sample to be suctioned and discharged.

3. Operation of the Dispensing Part

As shown in FIG. 8A, in the embodiment sample dispensation is performed by the first nozzle 111 and second nozzle 121; however, since the operation related to the first nozzle 111 and the operation related to the second nozzle 121 are performed with overlapping timing it is possible to reduce the time required for sample processing. The operation related to the first nozzle 111 and the operation related to the second nozzle 121 are described below referring to FIG. 9A through FIG. 12C. In the operations described below, the controller 280 performs controls of the first drive part 112, second drive part 122, pressure sources 151, 152, and 153, valves 155a, 155b and the like.

Figure 9A:
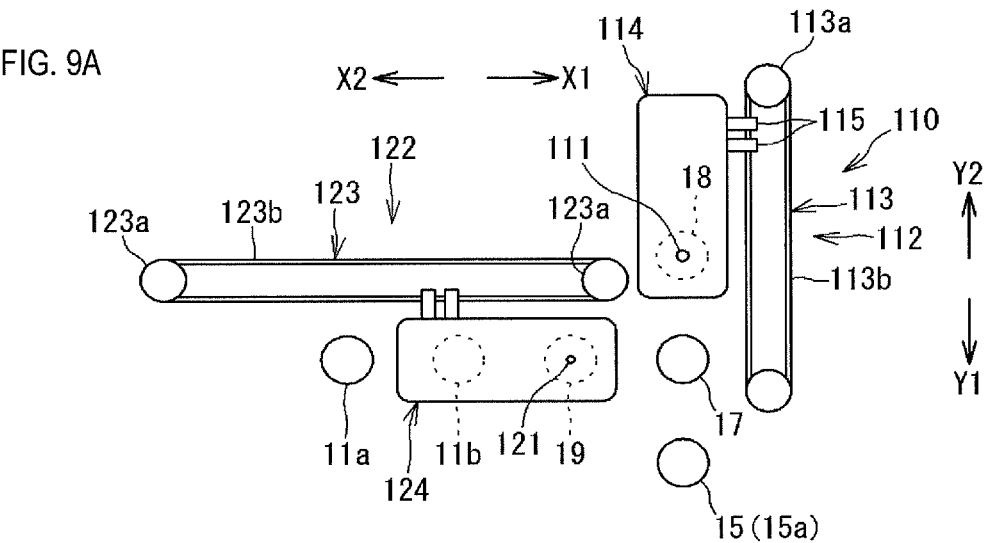
FIGS. 9A and 9B illustrate the positions of the first nozzle and the second nozzle.

In the standby state before sample measurement begins, the first nozzle 111 and second nozzle 121 are positioned at the initial positions shown in FIG. 9A. In the standby state, the first nozzle 111 is positioned above the first wash tank 18, and the second nozzle is positioned above the second wash tank 19. Note that in FIG. 6 the initial position of the first nozzle 111 is represented by the symbol 301a, and the initial position of the second nozzle 121 is represented by the symbol 302a.

Figure 9B:
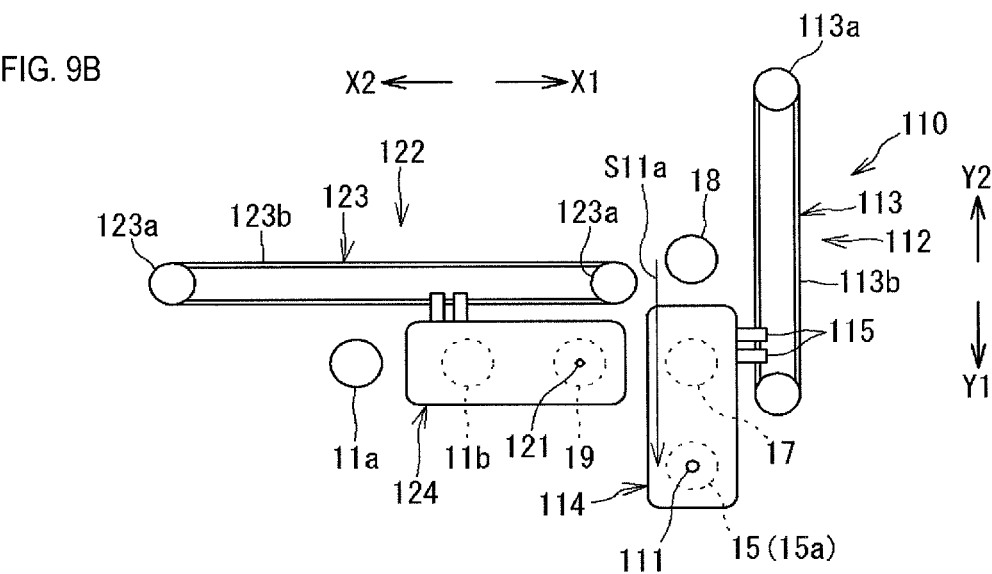

When the sample measurement begins, the first nozzle 111 is moved from the initial position 301a to the sample suctioning position 15a in step S11 shown in FIG. 8A. Step S11 includes steps S11a and S11b shown in FIG. 6. In step S11a, the first drive part 112 moves the first nozzle 111 forward in the Y1 direction, and positions the first nozzle 111 above the sample container 15 which is set at the sample suction position 15a, as shown in FIG. 9B. Then, in step S11b, the first nozzle 111 descends and enters the sample container 15. In this state, step S12 shown in FIG. 8A is performed. In step S12, the sample within the sample container 15 is suctioned and discharged by the mixing nozzle 111c by the pressure source connected to the mixing nozzle 111c of the first nozzle 111. The sample can be mixed within the sample container in this way. After mixing the sample, the sample within the sample container 15 is suctioned by the suction nozzle 111b by the pressure source connected to the suction nozzle 111b of the first nozzle 111. The amount of sample suctioned by the suction nozzle 111b is, for example, 450 µL.

When the suctioning of the sample is completed in step S12, the first nozzle 111 is moved from the position of the sample container 15 to the position of the holding chamber 17 in step S13. Step S13 includes steps S13a, S13b, and S13c shown in FIG. 6. In step S13a, the first nozzle 111 is raised and retracted from the sample container 15. Then, in step S13b the first drive part 112 moves the first nozzle 111 backward in the Y2 direction, and positions the first nozzle 111 above the holding chamber 17, as shown in FIG. 10A. Then, in step S13c the first nozzle 111 descends and enters the holding chamber 17. In this state, step S14 shown in FIG. 8A is performed. In step S14, the total amount of suctioned sample is discharged from the suction nozzle 11b of the first nozzle 111 into the holding chamber 17 by the pressure source 151.

During the above operation of the first nozzle 111, the second nozzle 121 is positioned above the second wash tank 19 and does not inhibit the movement of the first nozzle 111 above the first moving path 301.

When the discharging of sample is completed in step S14, the first nozzle 111 is moved from the position of the holding chamber 17 to the position of the first wash tank 18 in step S15. Step S15 includes steps S15a, S15b, and S15c shown in FIG. 6. In step S15a, the first nozzle 111 is raised and retracted from the holding chamber 17. Then, in step S15b the first horizontal mover 113 moves the first nozzle 111 backward in the Y2 direction and positions the first nozzle 111 above the first wash tank 18, as shown in FIG. 10B. Then, in step S15c the first nozzle 111 descends and enters the first wash tank 18. In this state, step S16 shown in FIG.

8A is performed. In step S16, the first nozzle 111 is washed in the first wash tank 18 by the wash liquid supplied from the wash liquid supplier 40. Thus, in the embodiment the controller 280 performs controls to move the first nozzle 111 to the position of the first wash tank 18 by the first drive part 112 and then wash the first nozzle 111 in the first wash tank 18 after the first nozzle 111 has discharged the sample into the holding chamber 17. When the washing of step S16 ends, the first nozzle 111 is raised and returned to the initial position 301a, and the standby state shown in FIG. 9A is restored in step S17. Steps S11 through S17 above are a first cycle of sample suctioning and discharging performed by the first nozzle 111. After the first cycle, a second cycle is executed to suction the sample of the next sample container 15.

When the first nozzle 111 is returned to the first wash tank 18 side in step S15b, the space above the holding tank 17 is empty. Therefore, the second nozzle 121 can move to a position above the holding chamber 17. In step S21 shown in FIG. 8A, step S21 in which the second nozzle 121 moves to the position of the holding chamber 17 is performed without waiting for the completion of step S16 in which the first nozzle 111 is washed. Step S21 includes steps S21a and S21b shown in FIG. 6. Step S21a begins when the first nozzle 111 starts moving to the first wash tank 18 in step S15. In step S21a, the second drive part 122 moves the second nozzle 121 to the right in the X1 direction, and positions the second nozzle 121 above the holding chamber 17, as shown in FIG. 10B. Then, in step S21b the second nozzle 121 descends and enters the holding chamber 17. In this state, step S22 shown in FIG. 8A is performed. Step S22 begins at substantially the same time with the start of washing of the first nozzle 111 in step S16. In step S22, part of the sample in the holding chamber 17 is suctioned from the second nozzle 121 by the pressure source 153 connected to the second nozzle 121. The amount of sample suctioned by the second nozzle 121 is, for example, 250 µL. Part of the sample is not suctioned and remains in the holding chamber 17. The remaining sample is used in conductivity measurement. Note that in step S22 part of the suctioned sample is discharged into the holding chamber 17 after sample is suctioned by the second nozzle 121, and the condition of sample filling to the bottom end of the second nozzle 121 is obtained in this way. Therefore, dispensing to the processing chambers 11a and 11b is performed more accurately.

When the suctioning of sample is completed in step S22, the second nozzle 121 is moved from the position of the holding chamber 17 to the position of the first processing chamber 11a in step S23. Step S23 includes steps S23a, S23b, and S23c shown in FIG. 6. In step S23a, the second nozzle 121 is raised and retracted from the holding chamber 17. Then, in step S23b the second drive part 122 moves the second nozzle 121 to the left in the X2 direction, and positions the second nozzle 121 above the first processing chamber 11a, as shown in FIG. 10C. Then, in step S23c the second nozzle 121 descends and enters the first processing chamber 11a. In this state, step S24 shown in FIG. 8A is performed. In step S24, part of the sample suctioned by the second nozzle 121 is discharged from the second nozzle 121 into the first processing chamber 11a by the pressure source 153. The amount of sample discharged into the first processing chamber 11a is, for example, 125 µL. In the first processing chamber 11a, the dispensed sample is mixed with first reagents 15a and 14a to prepare a first measurement sample.

Figure 11A:
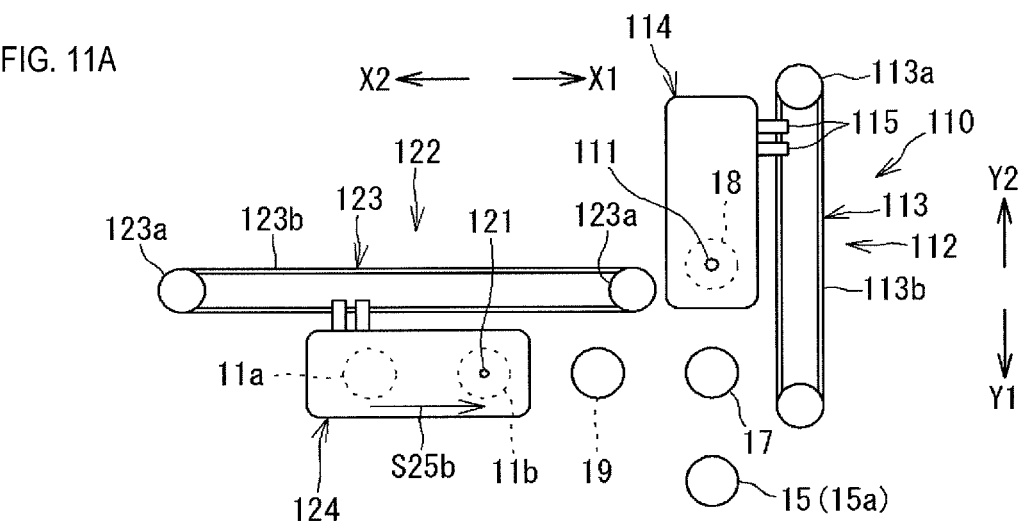
FIGS. 11A and 11B illustrate the positions of the first nozzle and the second nozzle.

After the sample is discharged into the first processing chamber 11a, the second nozzle 121 is moved from the position of the first processing chamber 11a to the position of the second processing chamber 11b in step S25. Step S25 includes steps S25a, S25b, and S25c shown in FIG. 6. In step S25a, the second nozzle 121 is raised and retracted from the first processing chamber 11a. Then, in step S25b the second drive part 122 moves the second nozzle 121 to the right in chamber 11b, as shown in FIG. 11A. The second nozzle 121 briefly waits at a position above the second processing chamber 11b. Then, in step S25c the second nozzle 121 descends and enters the second processing chamber 11b. In this state, step S26 shown in FIG. 8A is performed. In step S26, another part of the sample suctioned by the second nozzle 121 is discharged from the second nozzle 121 into the second processing chamber 11b by the pressure source 153. The amount of sample discharged into the second processing chamber 11b is, for example, 125 µL. In the second processing chamber 11b, the dispensed sample is mixed with second reagents 15b and 14b to prepare a second measurement sample.

In this way, in the embodiment the controller 280 performs controls to move the second nozzle 121 to the plurality of processing chambers 11a and 11b by the second drive part 122 and then discharge part of the sample from the second nozzle 121 into the respective plurality of processing chambers 11a and 11b during the time after the start of movement by the first nozzle 111 to the position of the first wash tank 18 until the first nozzle 111 suctions sample from the next sample container 15.

That is, in the embodiment the suctioning of sample from the holding chamber 17 by the second nozzle 121 is performed in parallel with the washing of the first nozzle 111 in step S16 shown in FIG. 8A. Moreover, moving the second nozzle 121 to the first processing chamber 11a in step S23, dispensing into the first processing chamber 11a by the second nozzle 121 in step S24, and moving the second nozzle 121 in steps S25a and S25b, are performed during step S16. Therefore, at least part of the operation of dispensing sample to the plurality of processing chambers 11a and 11b is performed while the first nozzle 111 is being washed in step S16. The first nozzle 111 is on standby at the initial position 301a above the first wash tank 18 until suctioning sample from the next sample container 15 in step S17 after the first nozzle 111 is washed in step S16. The remaining operations of dispensing sample to the plurality of processing chambers 11a and 11b are performed in step S17. That is, moving the movement of the second nozzle 121 in step S25c and dispensing by the second nozzle 121 into the second processing chamber 11b in step S26 are performed during step S17. In the embodiment, the above parallel processing is performed during the time taken to wash the first nozzle 111 in step S16. Contamination of the next sample suctioned by the first nozzle 111 is more reliably prevented by taking time to wash the first nozzle 111.

In the embodiment re-passing the second nozzle 121 over the processing chamber to which sample has already been discharged is prevented by performing the discharge from the second nozzle 121 into the plurality of processing chamber 11a and 11b with the first discharge to the processing chamber 11a which is positioned farthest from the holding chamber 17. For example, when sample is discharged to the first processing chamber 11a after first discharging sample to the second processing chamber 11b, the second nozzle 121 must re-pass over the second processing chamber 11b after discharging sample to the first processing chamber 11a. At this time there is a possibility that a slight residual sample remaining on the second nozzle 121 may fall into the second processing chamber 11b.

However, such an occurrence can be prevented by discharging sample from the second nozzle 121 first to the processing chamber 11a which is positioned farthest from the holding chamber 17.

Figure 11B:
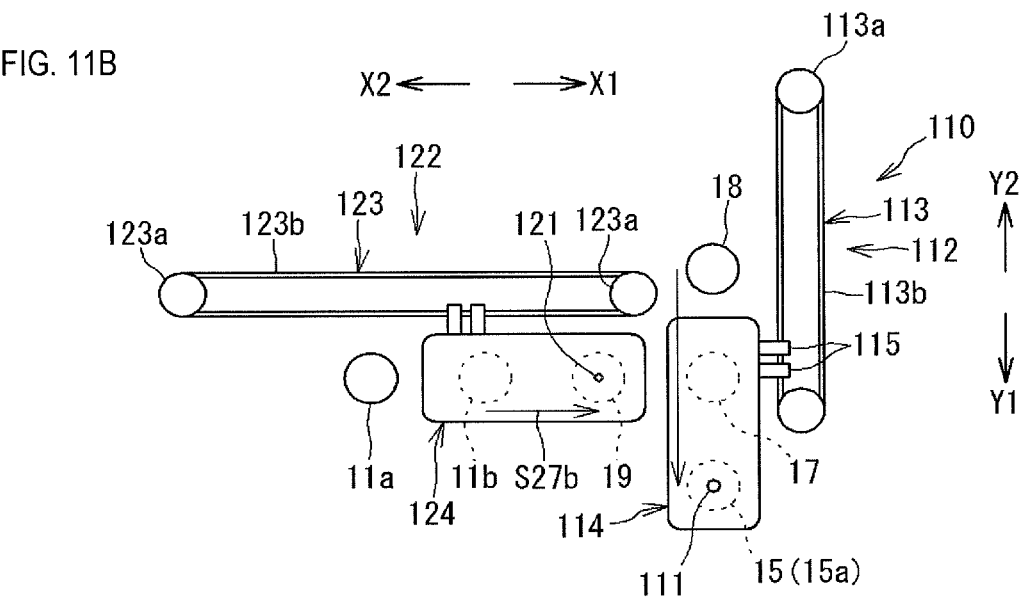

Following step S26, the second nozzle 121 is moved from the position of the second processing chamber 11b to the position of the second wash tank 19 in step S27. Step S27 includes steps S27a, S27b, and S27c shown in FIG. 6. In step S27a, the second nozzle 121 is raised and retracted from the second processing chamber 11b. Then, in step S27b the second drive part 122 moves the second nozzle 121 to the right in the X1 direction, and positions the second nozzle 121 above the second wash tank 19, as shown in FIG. 11B. Then, in step S27c the second nozzle 121 descends and enters the second wash tank 19. In this state, step S28 shown in FIG. 8A is performed. In step S28, the second nozzle 121 is washed in the second wash tank 19 by the wash liquid supplied from the wash liquid supplier 40. Thus, in the embodiment the controller 280 performs controls to move the second nozzle 121 to the position of the second wash tank 19 by the second drive part 122 and wash the second nozzle 121 in the second wash tank 19 after the second nozzle 121 has discharged the sample into the plurality of processing chambers 11a and 11b.

When the washing of step S28 ends, the second nozzle 121 is raised and returned to the initial position 302a, and the standby state shown in FIG. 9B is restored, in step S29. Steps S21 through S29 above are a first cycle of sample suctioning and discharging performed by the second nozzle 121. After the first cycle, a second cycle is executed to suction the sample of the next sample container 15 which is held in the holding chamber 17.

As shown in FIG. 8A, in the embodiment controls are executed to move the first nozzle 111 to the next sample container 15, suction the next urine sample, and discharge the suctioned sample into the holding tank 17 after the second nozzle 121 has been moved to the second wash tank 19. As a result, washing of the second nozzle 121 in step S28 and step S12 of the second cycle pertaining to the sample of the next sample container 15 are performed with overlapping timing. This occurs during the time of washing the second nozzle 121 in step S28. Contamination of the next sample suctioned by the second nozzle 121 is more reliably prevented by taking time to wash the second nozzle 121.

The time required for sample processing is increased as shown in FIG. 8B when sample is dispensed from the sample container 15 to the processing chambers 11a and 11b using a single nozzle and the dispensing part 200 does not have the plurality of nozzles 111 and 121 and holding chamber 17 of the embodiment. That is, when sample is suctioned from the sample container 15 and sample is discharged to the processing chambers 11a and 11b by a single nozzle, suctioning of the sample contained in the next sample container 15 cannot be performed until completion of washing the nozzle following sample discharge into the processing chambers 11a and 11b. An example of the sample processing sequence when using a single nozzle is shown in FIG. 8B. In FIG. 8B, the nozzle is moved from the initial position to the sample suction position in step S41. The operation performed in step S41 is identical to the operation performed in step S11. The, in step S42 sample is suctioned by the nozzle. The operation performed in step S42 is identical to the operation performed in step S12. In step S43, the nozzle is moved to the wash tank. In step S44, part of the suctioned sample is discharged from the nozzle into the wash tank to fill the bottom of the nozzle with sample.

In step S45 to step S49, the nozzle is moved to the position of the processing chamber and discharges sample into the processing chamber, then is moved to the position of the wash tank. The operations of steps S45 through S49 are identical to the operations of steps S23 through S27. In step S50, the nozzle is washed in the wash tank, and returned to the initial position in step S51. The operations of steps S50 and S51 are identical to the operations of steps S16 and S17. Steps S41 through S51 above are a first cycle of sample suctioning and discharging performed by the single nozzle. After the first, cycle, a second cycle is executed to suction the sample of the next sample container 15. In the example of FIG. 8B, there is an increase in the time required since step S41 of the second cycle cannot be executed until step S50 of the first cycle is completed. The completion of washing the nozzle after dispensing sample is especially delayed due to the increase in time required to dispense the sample when sample must be dispensed to a plurality of processing chambers.

Conversely, in the embodiment the time is reduced since the first nozzle 111 also discharges sample to a single holding chamber 17 which is disposed near the position of the sample container 15 after the sample nozzle 111 has suctioned sample from the sample container 15 in step S11, compared to dispensing to a plurality of processing chambers 11a and 11b. In the example of FIG. 8B, when there is a partial discharge of the sample to the sample container in step S44, the discharged sample enters the sample container. To use the residual sample in the sample container in a separate analysis, the sample suctioned by the nozzle which does not temporarily enter the sample container is suitable for separate analysis. In the case of a single nozzle, therefore, it is desirable to move the nozzle to the wash tank to partially discharge the sample after the sample has been suctioned from the sample container. However, the operations of steps S43 and S44 are unnecessary due to the partial discharge of sample into the holding chamber 17 in step S22 of the embodiment.

As mentioned previously, part of the sample remains and is not suctioned from the holding chamber 17 in step S22 of FIG. 8A. In step S31 of FIG. 8A, the sample remaining in the holding chamber 17 is drawn to the conductivity measuring part 275 through the flow path 41, and the conductivity of the sample is measured. Since the conductivity of the urine sample is used to determine the specific gravity of the urine, a suitable conductivity can be determined by measuring the original sample before the sample is mixed with a reagent, and not a measurement sample to which reagent has been added. That is, although it is desirable to use a measurement sample in which the sample is processed by a reagent when masking optical measurements using a flow cell, it also is desirable to use the original sample before it is mixed with reagent when the measurement is for analyzing the sample as in the case of conductivity. Accordingly, in measurements where it is desirable to use the original sample before it is mixed with reagent as in the case of conductivity, a suitable measurement is possible by measuring the sample remaining in the holding chamber 17.

After the conductivity measurement in step S31, the holding chamber 17 is washed by wash liquid supplied from the wash liquid supplier 40 in step S32. Thus, the next sample can be discharged from the first nozzle 111 to the holding chamber 17.

Figure 12A:
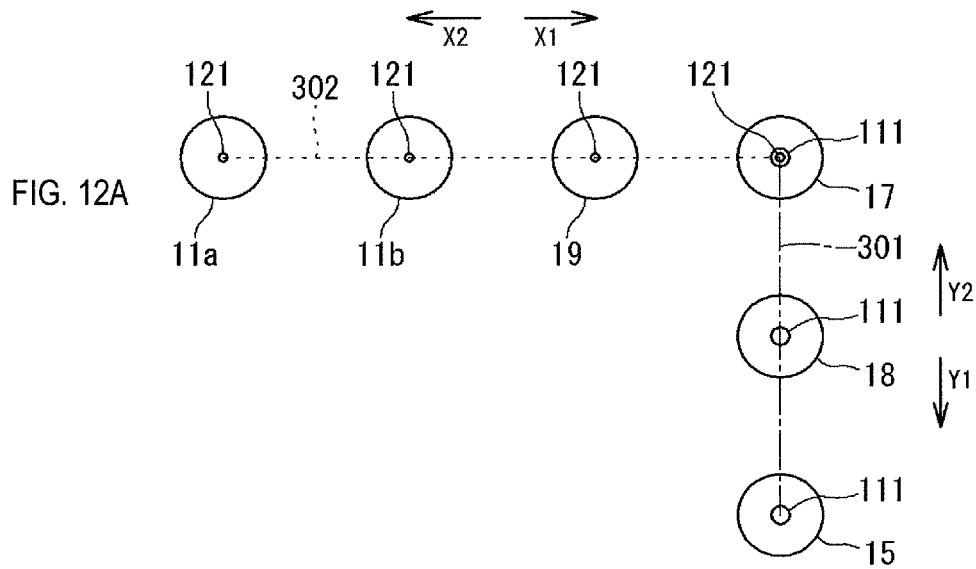
FIGS. 12A, 12B and 12C illustrate the layout of the holding chamber, processing chambers, and wash tanks.
Figure 12B:
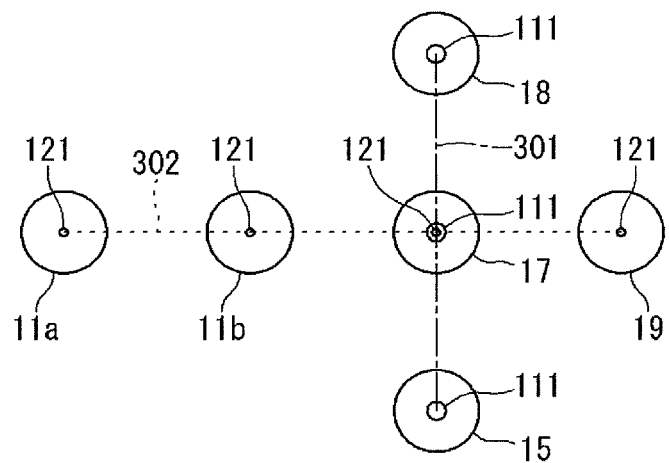

4. Modifications of the Holding Chamber, Processing Chamber, and Wash Tank Layout The layout of the holding chamber, processing chambers, and wash tanks is not limited to the layout shown in FIG. 6 inasmuch as the layout shown in FIGS. 12A-12B is also possible. Although the first moving path 301 and second moving path 302 are T-shaped in entirety in FIG. 6, the first moving path 301 and second moving path 302 are L-shaped shown in FIG. 12A. In FIG. 12A the first moving path 301 and second moving path 302 are perpendicular, and the holding chamber 17 is disposed at the intersection of the first moving path 301 and second moving path 302. In FIG. 12A the first wash tank 18 is disposed between the sample container 15 and the holding chamber 17. In the layout shown in FIG. 12A, the distance is increased between the sample container 15 and the holding chamber 17.

The first moving path 301 and second moving path 302 shown in FIG. 12B are cross-shaped. In the layout shown in FIG. 12B, the second wash tank 19 is disposed on the right side, that is, on the X1 direction side of the holding chamber 17, and not between the holding chamber 17 and the second processing chamber 11b.

Figure 12C:
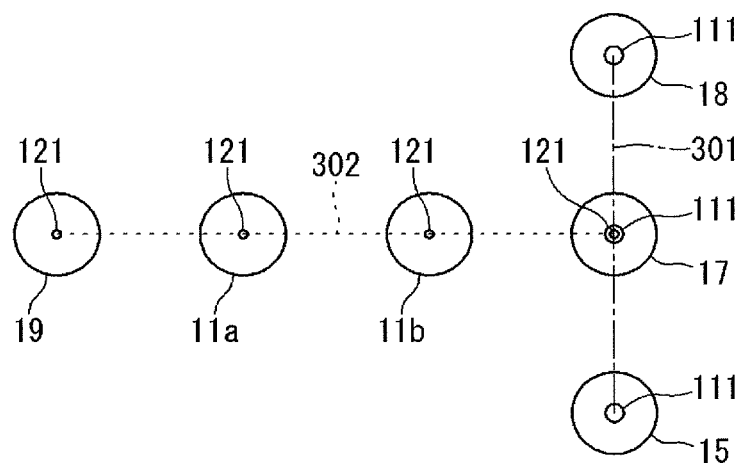

The first moving path 301 and second moving path 302 shown in FIG. 12C is T-shaped identically to FIG. 6. However, the second wash tank 19 is disposed at a position farther from the processing chambers 11a and 11b viewed from the holding chamber 17.

What is claimed is:

1. A urine sample analyzer comprising:
   a first nozzle configured to suction a urine sample from a sample container and to move in a first movement path;
   a holding chamber located on the first movement path and configured to receive the urine sample discharged by the first nozzle;
   a first wash tank located on the first movement path for washing the first nozzle;
   a second nozzle configured to suction the urine sample from the holding chamber and to move in a second movement path;
   a plurality of processing chambers located on the second movement path and configured to receive the urine sample discharged by the second nozzle and to process the discharged urine sample,
   a processor programmed to:
     cause the first nozzle to move to the first wash tank for washing the first nozzle in the first wash tank after the first nozzle has discharged a urine sample into the holding chamber; and
     cause the second nozzle to move to the holding chamber after the first nozzle has started moving from the holding chamber to the first wash tank, cause the second nozzle which has suctioned the urine sample to move from the holding chamber to each of the plurality of processing chambers, and cause the second nozzle to discharge a part of the urine sample into each of the plurality of processing chambers;
   a detector configured to detect information of material components in the urine samples respectively processed in the plurality of processing chambers; and
   an analyzing part configured to analyze the information of the material components detected by the detector,
   wherein the first movement path intersects with the second movement path; and
   the holding chamber is at an intersection point of the first movement path and the second movement path.

2. The urine sample analyzer of claim 1, wherein the holding chamber is closer to the sample container than the first wash tank on the first movement path.

3. The urine sample analyzer of claim 2, wherein the first movement path orthogonally intersects with the second movement path.

4. The urine sample analyzer of claim 1, further comprising:
   a second wash tank on the second movement path for washing the second nozzle;
   wherein the processor is further programmed to cause the second nozzle to move to the second wash tank for washing the second nozzle in the second wash tank after the second nozzle discharges part of the urine sample to each of the plurality of processing chambers.

5. The urine sample analyzer of claim 4, wherein the second wash tank is at a position closer to the holding chamber than any processing chamber among the plurality of processing chambers.

6. The urine sample analyzer of claim 4, wherein the processor is further programmed to cause the first nozzle to move to a next sample container to suction a next urine sample and discharge the suctioned next urine sample into the holding chamber after the second nozzle has been moved to the second wash tank.

7. The urine sample analyzer of claim 1, wherein the processor is programmed to cause the second nozzle to discharge the urine sample first into the processing chamber disposed farthest away from the holding chamber among the plurality of processing chambers.

8. The urine sample analyzer of claim 1, wherein the holding chamber is closer to the sample container than any processing chamber among the plurality of processing chambers.

9. The urine sample analyzer of claim 1, wherein the plurality of processing chambers comprise a first processing chamber and a second processing chamber,
   the first processing chamber is configured to prepare a first measurement sample from a first reagent and a part of the urine sample discharged from the second nozzle, and
   the second processing chamber is configured to prepare a second measurement sample from a second reagent and another part of the urine sample discharged from the second nozzle.

10. The urine sample analyzer of claim 9, further comprising:
    sample introduction paths to direct measurement samples respectively prepared in the first processing chamber and second processing chamber to the detector-, wherein the detector comprises:
    a flow cell through which flows a measurement sample directed by the sample introduction path;
    a light irradiating part that irradiates light on the measurement sample flowing through the flow cell; and
    a light receiving part that receives light given off from the components in the measurement sample irradiated by light,
    wherein the analyzing part analyzes characteristic parameters of the light received by the light receiving part.

11. The urine sample analyzer of claim 10, further comprising a measuring part for measuring the urine sample held in the holding chamber, wherein the measuring part is configured to perform a measurement different from a measurement using the flow cell.

12. The urine sample analyzer of claim 11, wherein the measurement part is configured to measure electrical conductivity of the urine sample.

13. The urine sample analyzer of claim 1, further comprising a wash liquid supplier for supplying wash liquid to the holding chamber to wash the holding chamber.

14. The urine sample analyzer of claim 1, further comprising:
- a pressure source that generates pressure to suction and discharge the urine sample;
- a first flow path that connects the first nozzle to the pressure source;
- a second flow path that branches from the first flow path at a first position of the first flow path, and that conjoins with the first flow path at a second position on the pressure source side of the first position;
- a filter for capturing foreign matter in the urine sample, and in the first flow path between the first position and the second position; and
- valves that control a flow of fluid in a flow path circuit that includes the first flow path and the second flow path,
- wherein the processor is further programmed to control the valves so that the urine sample suctioned by the first nozzle passes through the filter, and the urine sample that has passed through the filter bypasses the filter by passing through the second flow path and is discharged from the first nozzle.

15. The urine sample analyzer of claim 1, wherein the processor further is programmed to control a discharge of the urine sample which has been suctioned from the sample container by the first nozzle back to the sample container in order to mix the urine sample in the sample container.

16. A urine sample analyzer comprising:
- a first nozzle configured to be movable in a first movement path and suction a urine sample from a sample container located on the first movement path;
- a first wash tank located on the first movement path for washing the first nozzle;
- a holding chamber located on the first movement path between the sample container and the first wash tank, and configured to receive the urine sample discharged by the first nozzle;
- a second nozzle configured to suction the urine sample from the holding chamber and be movable in a second movement path;
- a processing chamber located on the second movement path and configured to receive the urine sample discharged by the second nozzle to process the discharged urine sample;
- a second wash tank located on the second movement path between the holding chamber and the processing chamber for washing the second nozzle;
- a detector for detecting information of material components in the urine samples processed in the processing chamber; and
- an analyzing part for analyzing the information of material components detected by the detector;
- wherein the first movement path intersects with the second movement path,
- the holding chamber is at an intersection point of the first movement path and the second movement path, and
- the holding chamber is closer to the sample container than the first wash tank in the first movement path.

17. The urine sample analyzer of claim 16, wherein the first movement path orthogonally intersects with the second movement path.

18. The urine sample analyzer of claim 16, wherein the second wash tank is closer to the holding chamber than the processing chamber.

19. The urine sample analyzer of claim 16, wherein the holding chamber is closer to the sample container than the processing chamber.

* * * * *